US00PP12820P2

(12) United States Plant Patent
van Rijn

(10) Patent No.: US PP12,820 P2
(45) Date of Patent: Jul. 30, 2002

(54) ANTHURIUM PLANT NAMED 'RED MIRACLE'

(75) Inventor: Leonardus W. B. M. van Rijn, Schipluiden (NL)

(73) Assignee: RijnPlant B.V., Schipluiden (NL)

( * ) Notice: Subject to any disclaimer, the term of this patent is extended or adjusted under 35 U.S.C. 154(b) by 0 days.

(21) Appl. No.: 09/837,572

(22) Filed: Apr. 18, 2001

(51) Int. Cl.[7] ..... A01H 5/00

(52) U.S. Cl. ..... Plt./369
(58) Field of Search ..... Plt./369

*Primary Examiner*—Bruce R. Campell
*Assistant Examiner*—A Para
(74) *Attorney, Agent, or Firm*—C. A. Whealy

(57) ABSTRACT

A distinct cultivar of Anthurium plant named 'Red Miracle', characterized by its upright and somewhat outwardly spreading plant habit; dark green leaves; dark red-colored spathes with dark purplish red-colored spadices that are positioned upright and beyond the foliage on strong and erect scapes; and good inflorenscence longevity.

2 Drawing Sheets

BACKGROUND OF THE INVENTION

The present invention relates to a new and distinct cultivar of Anthurium plant, botanically known as *Anthurium andreanum*, and hereinafter referred to by the name 'Red Miracle'.

The new Anthurium is a product of a planned breeding program conducted by the Inventor in Schipluiden, The Netherlands. The objective of the program is to create and develop new freely flowering Anthurium cultivars that have strong roots, dark green leaves, attractive spathe color, and good inflorescence longevity.

The new Anthurium is a naturally-occurring whole plant mutation of the *Anthurium andreanum* cultivar Leny, disclosed in U.S. Plant Pat. No. 10,272. The new Anthurium was discovered and selected by the Inventor as a single plant within a population of plants of the cultivar Leny in a controlled environment in Schipluiden, The Netherlands in September, 1998. The new Anthurium was selected on the basis of its thick petioles and spadices.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Red Miracle. These characteristics in combination distinguish 'Red Miracle' as a new and distinct cultivar:

1. Upright and somewhat outwardly spreading plant habit.
2. Dark green leaves.
3. Dark red-colored spathes with dark purplish red-colored spadices that are positioned upright and beyond the foliage on strong and erect scapes.

4. Freely flowering habit.
5. Good inflorescence longevity.

The new Anthurium can be compared to the parent, the cultivar Leny. In side-by-side comparisons conducted in Schipluiden, The Netherlands, plants of the new Anthurium differ from plants of the cultivar Leny in the following characteristics:

1. Plants of the new Anthurium have longer and narrower leaves than plants of the cultivar Leny.
2. Plants of the new Anthurium have thicker petioles than plants of the cultivar Leny.
3. Plants of the new Anthurium have thicker spadices than plants of the cultivar Leny.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical potted plant of the cultivar Red Miracle that was about three years old.

The photograph at the top of the second sheet comprises a close-up view of a typical inflorescence of 'Red Miracle'.

The photograph at the bottom of the second sheet comprises a close-up view of a typical leaf of 'Red Miracle'.

DETAILED BOTANICAL DESCRIPTION

In the following description, color references are made to The Royal Horticultural Society Colour Chart except where general terms of ordinary dictionary significance are used. The following observations and measurements describe 3-year old plants grown in 19-cm containers in Schipluiden, The Netherlands, in a glass greenhouse with an average day temperature of 25° C. and an average night temperature of 19° C.

Botanical classification: *Anthurium andreanum* cultivar Red Miracle.

Parentage: Naturally-occurring whole plant mutation of *Anthurium andreanum* cultivar Leny, disclosed in U.S. Plant Pat. No. 10,272.

Propagation:

*Method.*—By tissue culture.

*Time to develop roots on a tissue-cultured cutting.*—About 70 or 84 days at 24° C. or 21° C., respectively.

*Root description.*—Strong fleshy roots.

Plant description:

*Plant shape.*—Upright and somewhat outwardly spreading, inverted triangle, symmetrical.

*Growth habit.*—Freely clumping, bushy and dense. Appropriate for 13 to 35-cm containers. Vigorous.

*Plant height.*—About 70 to 95 cm.

*Crop time.*—About 10 months are usually required from planting of young plants to finished plants in a 17-cm container.

*Foliage description.*—Quantity per plant: About 70 to 80. Length: About 19 to 35 cm. Width: About 11 to 18 cm. Shape: Cordate. Apex: Apiculate. Base: Auriculate; lobes not overlapping. Margin: Entire. Texture: Smooth, glabrous, leathery. Venation pattern: Pinnate. Color: Young leaves, upper surface: 147A. Young leaves, lower surface: 147B to 147C. Mature leaves, upper surface: 137A to 147A; venation, 146B. Mature leaves, lower surface: 144B to 146D; venation, 146C. Petiole: Length: About 25 to 55 cm. Color: 146C. Geniculum length: About 2 to 3 cm. Geniculum color: 146C.

Inflorescence description:

*Inflorescence arrangement.*—Spathes with spadices held beyond the foliage. Flowering structures arise from leaf axils. Freely and continuous flowering year-round; typically more than 30 inflorescences per plant.

*Inflorescence longevity.*—Inflorescences last about six weeks under winter conditions and about three months under summer conditions; persistent.

*Spathe.*—Length: About 9 to 14 cm. Width: About 8 to 12 cm. Shape: Cordate. Apex: Apiculate to mucronulate. Base: Auriculate; lobes not overlapping. Margin: Entire. Texture: Leathery, glabrous, some blistering. Color: When opening: 53A to 53B, glossy. Opened, front surface: 45A, glossy. Opened, back surface: 45B, glossy.

*Spadix.*—Length: About 7 to 11 cm. Diameter: About 1 to 2 cm. Shape: Columnar. Cross section: Rounded. Longitudinal axis: Erect. Color: Immature: 146D. Mature: 60A.

*Flowers.*—Quantity per spadix: Numerous, about 400. Shape: Rounded. Diameter: About 2 mm, maximum.

*Reproductive organs.*—Androecium: Pollen color: 159B. Gynoecium: Stigma shape: Ovoid.

*Scape.*—Length: About 43 to 70 cm. Aspect: Strong and erect. Color: 183B.

*Seed.*—Seed development on plants of the new Anthurium has not been observed.

Disease/pest resistance: Under commercial conditions, plants of the new Anthurium have not been observed to be resistant to pathogens or pests common to Anthurium.

It is claimed:

1. A new and distinct cultivar of Anthurium plant named 'Red Miracle', as illustrated and described.

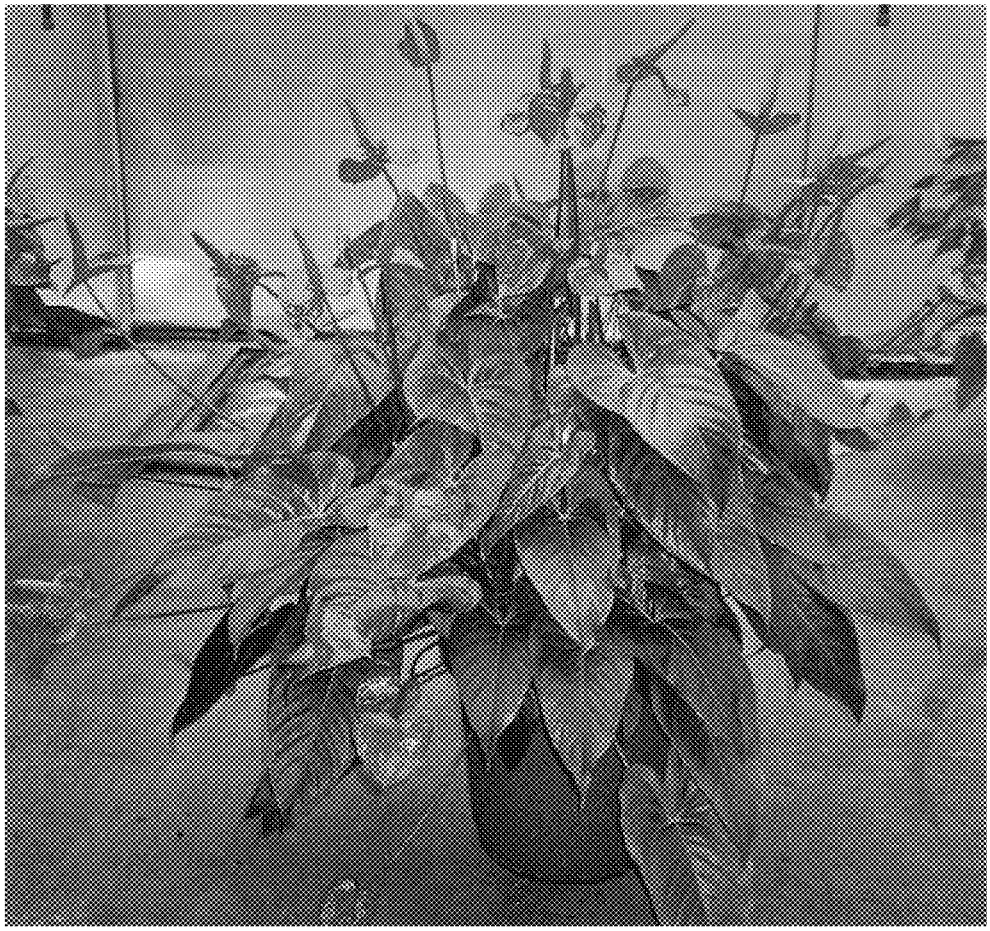

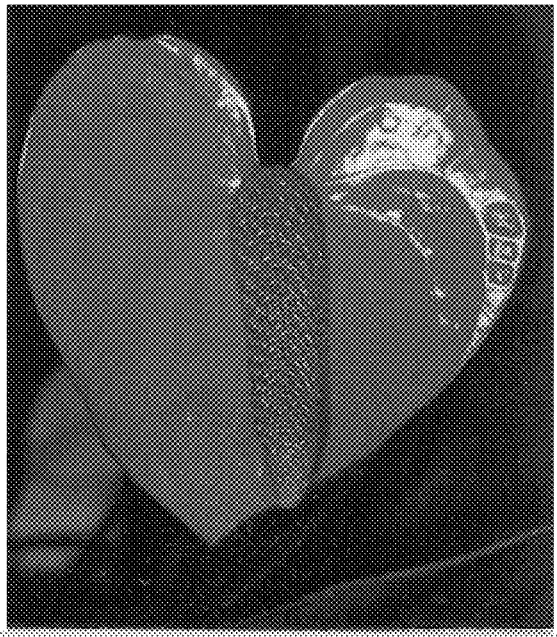
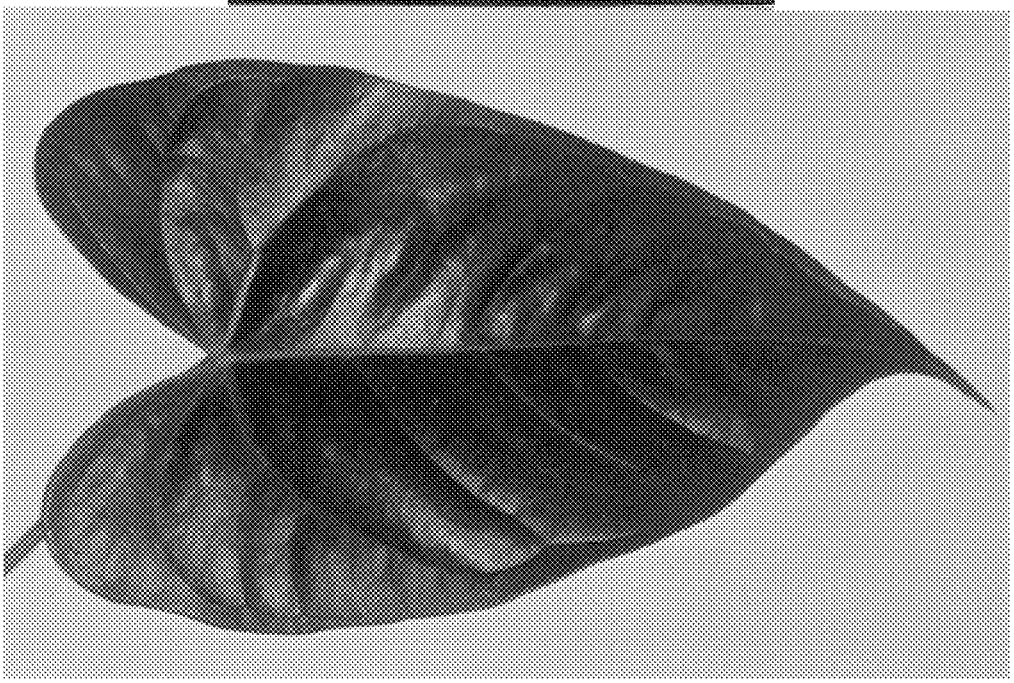

* * * * *